United States Patent [19]
Pinosky

[11] Patent Number: 5,622,167
[45] Date of Patent: Apr. 22, 1997

[54] METHOD AND DEVICE FOR RELIEVING RESPIRATORY DISTRESS DURING PATIENT TRANSPORT

[76] Inventor: Mark L. Pinosky, 536 Overseer Retreat, Mount Pleasant, S.C. 29464

[21] Appl. No.: 644,106

[22] Filed: May 10, 1996

[51] Int. Cl.⁶ .................................................. A61M 16/04
[52] U.S. Cl. ...................................... 128/207.14; 604/317
[58] Field of Search ......................... 128/207.14; 604/73, 604/319

[56] References Cited

U.S. PATENT DOCUMENTS 4,915,691  4/1990  Jones et al. ............................ 128/14

*Primary Examiner*—Vincent Millin
*Assistant Examiner*—Robert N. Wieland
*Attorney, Agent, or Firm*—B. Craig Killough

[57] ABSTRACT

A manually operated and portable device for relieving respiratory distress caused by blockage of an endotracheal tube, and a method of using the device. A manually operated suction device is connected to a suction catheter, and the suction catheter is inserted intraluminally into the endotracheal tube. The suction device is manually actuated to remove the blockage.

13 Claims, 1 Drawing Sheet

METHOD AND DEVICE FOR RELIEVING RESPIRATORY DISTRESS DURING PATIENT TRANSPORT

FIELD OF THE INVENTION

This invention relates to medical devices generally, and is more particularly related to a portable, manually operated suction device which is connected to an endotracheal tube for relieving respiratory distress, and a method of using same.

BACKGROUND OF THE INVENTION

Tracheal intubation is used to relieve respiratory distress. It is well known to use mechanical ventilators in association with tracheal intubation. Vacuum pumps which are available in medical facilities provide readily available vacuum or suction. Access to the vacuum or suction provided by these large vacuum pumps is available at multiple outlets provided throughout health care facilities. Catheters may be connected to the suction at available wall outlets. The force of the suction available at such outlets may be varied according to need, but suction measured at approximately 560 mmHg is generally available.

Suction or vacuum which is available through a central system is limited, in that it is not portable. In the event a patient needs to be transported from room to room within the facility, it is not practical to connect vacuum or suction lines to the wall suction and to the patient. Prior to the present invention, either cumbersome electrically operated suction devices must be transported with the patient, or the patient is placed at risk during transportation from, for example, an intensive care unit to an operating room.

SUMMARY OF THE PRESENT INVENTION

The present invention is a method and device for relieving respiratory distress on an emergency basis during patient transport. One end of a suction catheter is inserted into the patient's respiratory tree. A syringe is attached to the opposite end of the suction catheter, and air is evacuated from the catheter into the syringe, by causing a piston in the syringe to traverse a cylinder of the syringe, to draw air from the catheter into the syringe.

DESCRIPTION OF THE PREFERRED EMBODIMENT

A hand-held, manually operated, means for creating a vacuum or a suction is provided. It is preferred that the means for creating a vacuum or suction be capable of creating a vacuum or suction pressure of not less than 500 mmHg.

Figure 1:
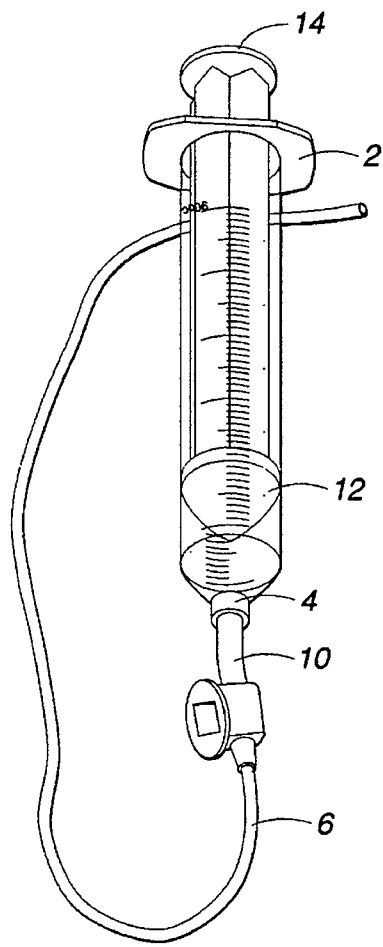
FIG. 1 is a perspective view of the device.
Figure 2:
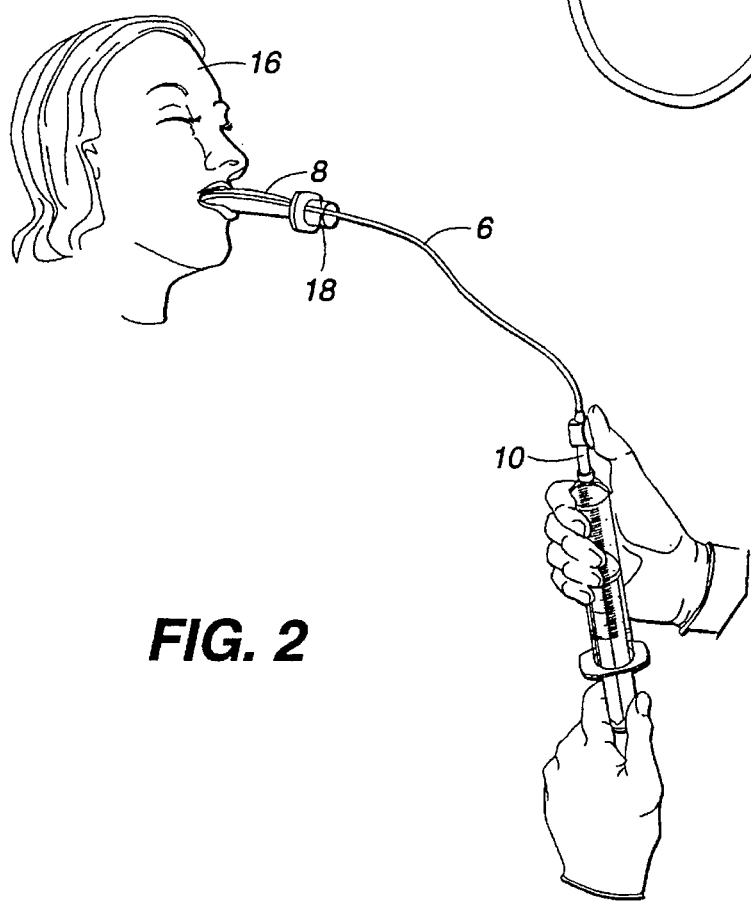
FIG. 2 is shows the device inserted into an endotracheal tube.

Referring now to the drawing figures, FIG. 1 shows a means for creating a vacuum or suction which is a syringe 2. The syringe is characterized by a cylinder and a piston 12 which traverses the cylinder. The piston will typically be formed of a resilient material which forms an air tight seal around the wall of the cylinder. The piston has a handle 14 which communicates with the piston, and which allows the piston to be manually actuated to traverse the cylinder. For most applications, the hand held means for creating a vacuum should produce a vacuum suction of not less than 500 mmHg when used as part of the invention. A 60 cc model syringe produced by Beckton Dickinson, Franklin Lake, N.J., will create a vacuum of approximately 600 mmHg in use. The pressure created by the device may be varied by the use of syringes having various bores, strokes and displacements, as required by the particular application.

The syringe 2 is connected at an end 4 to a suction catheter 6. It is preferred to use an intraluminal tube 8, which provides an endotracheal tube having a tube within a tube upon insertion of the suction catheter.

It is necessary to connect the syringe to the suction catheter so that there is no loss of vacuum or suction at the point of connection. It is preferred to have a syringe with a luer fitting 10 thereon which mounts to the suction catheter. The suction catheter may be directly mounted to the syringe by threaded means.

The syringe readily creates a manual, easily transportable means for creating the necessary vacuum. Other manually operated vacuum means which are capable of connection to a suction catheter could be used.

When a tracheal tube is inserted into the respiratory tree, the normal respiratory functions are changed. The patient 16 is completely dependent on the endotracheal tube 18 for ventilation and oxygenation. The inside diameters of endotracheal tubes vary from 2.5 to 9.0 min. This increases the risk to the patient of an obstruction in the tube due to inspissation of secretions.

The device is assembled by inserting one end of a suction catheter, of appropriate size for the corresponding endotracheal tube, onto a syringe. The device can then be inserted intraluminally through the endotracheal tube. Once it is fully inserted then suction can be applied via manual retraction on the syringe handle. Situations in which the device can be used include life threatening inability to ventilate or oxygenate the patient secondary to obstruction of the endotracheal tube. Materials and objects that may obstruct the tube include inspissated secretions, blood, foreign bodies, and gastric aspirations.

The invention provides a portable suction device which is light weight and is easily transportable. It is not necessary to provide external power sources, such as electrically or pneumatically powered suction devices. Risk to the patient from intrafacility transportation is reduced by the device and method.

What is claimed is:

1. A means for relieving respiratory distress due to a blockage
in an endotracheal tube using a hand held suction means, comprising the steps of:
   a. assembling a hand held suction device comprising a suction catheter and a suction means which is connected to said suction catheter, said suction means having suction generating means, wherein said suction generating means is held in a hand of a user and is manually operated and has no externally powered assistance;
   b. inserting one end of said suction catheter into an endotracheal tube and into a patient;
   c. creating a suction through said suction catheter by manually actuating said suction generating means; and
   d. removing a blockage of said endotracheal tube.

2. A hand held suction device for relieving respiratory distress, comprising:

a. a suction catheter;

b. suction means which is connected to said suction catheter, said suction means having suction generating means, wherein said suction generating means is held in a hand of a user, and said suction generating means is manually operated and has no externally powered assistance; and c. an endotracheal tube into which said suction catheter is inserted.

3. A hand held suction device for relieving respiratory distress as described in claim 2, wherein said suction means is a syringe.

4. A hand held suction device for relieving respiratory distress as described in claim 2, wherein said suction means is a syringe, and said syringe is connected to said suction catheter by a luer fitting.

5. A hand held suction device for relieving respiratory distress as described in claim 2, wherein said suction means creates a suction through said suction catheter of not less than 500 mmHg.

6. A hand held suction device for relieving respiratory distress as described in claim 3, wherein said syringe creates a suction through said suction catheter of not less than 500 mmHg.

7. A hand held suction device for relieving respiratory distress as described in claim 4, wherein said syringe creates a suction through said suction catheter of not less than 500 mmHg.

8. A hand held suction device for relieving respiratory distress, comprising:

a. a suction catheter;

b. suction means which is connected to said suction catheter, said suction means having suction generating means, wherein said suction generating means is held in a hand of a user, and said suction generating means is manually powered and creates a suction through said suction catheter of not less than 500 mmHg; and c. an endotracheal tube into which said suction catheter is inserted.

9. A hand held suction device for relieving respiratory distress as described in claim 8, wherein said suction means is a syringe.

10. A hand held suction device for relieving respiratory distress as described in claim 8, wherein said suction means is a syringe, and said syringe is connected to said suction catheter by a luer fitting.

11. A hand held suction device for relieving respiratory distress as described in claim 1, wherein said suction means is a syringe.

12. A hand held suction device for relieving respiratory distress as described in claim 1, wherein said suction means creates a suction through said suction catheter of not less than 500 mmHg.

13. A hand held suction device for relieving respiratory distress as described in claim 11, wherein said syringe creates a suction through said suction catheter of not less than 500 mmHg.

* * * * *